United States Patent [19] [11] 4,212,865
Scherrer et al. [45] Jul. 15, 1980

[54] AMINE DERIVATIVES OF 2-NITRO-3-PHENYLBENZOFURAN

[75] Inventors: Robert A. Scherrer, White Bear Lake; Richard M. Stern, Cottage Grove, both of Minn.; Vernon R. Fletcher, Davis, Calif.

[73] Assignee: Riker Laboratories, Inc., Northridge, Calif.

[21] Appl. No.: 973,153

[22] Filed: Dec. 26, 1978

[51] Int. Cl.² .................... A01N 9/20; C07D 307/82
[52] U.S. Cl. ................................ 424/250; 424/267; 424/274; 424/285; 260/326.1; 260/326 N; 260/326.5 CA; 260/326.8; 260/326.9; 260/346.73
[58] Field of Search ........... 260/346.73, 326 N, 326.1, 260/326.5 CA, 326.8, 326.9; 544/376; 546/196; 424/267, 250, 274, 285

[56] References Cited

U.S. PATENT DOCUMENTS

| 3,862,134 | 1/1975 | Scherrer | 260/346.22 |
| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |
| 4,124,704 | 11/1978 | Scherrer | 260/346.22 |

Primary Examiner—John M. Ford
Assistant Examiner—Bernard Dentz
Attorney, Agent, or Firm—Cruzan Alexander; Donald M. Sell; Donald C. Gipple

[57] ABSTRACT

2-Nitro-3-phenylbenzofurans wherein the benzo or 3-phenyl portion of the molecule is bonded directly to an optionally substituted amino group, which are active as antimicrobial agents and processes for their use.

24 Claims, No Drawings

AMINE DERIVATIVES OF 2-NITRO-3-PHENYLBENZOFURAN

BACKGROUND OF THE INVENTION

This invention relates to a class of 2-nitro-3-phenylbenzofuran compounds wherein the benzo or 3-phenyl portion of the molecule is bonded directly to an amino group. It also relates to the use of the compounds as antimicrobial agents.

Compounds wherein 2-nitro-3-phenylbenzofuran is substituted by certain neutral or acidic groups are known. See, for example, U.S. Pat. Nos. 4,022,908; 4,048,323; 4,066,782; 4,067,993 and 4,124,704. No previous disclosure of compounds wherein the benzo or 3-phenyl portions of 2-nitro-3-phenylbenzofurans is substituted by an amino group are known, however.

DETAILED DESCRIPTION OF THE INVENTION

The 2-nitro-3-phenylbenzofuran compounds of the invention are substituted on the benzo or 3-phenyl portion of the molecule by an amino group which is primary, secondary or tertiary or part of a cyclic amino and/or may be acylated or sulfonylated or may be part of a triazino group. These compounds have the formula

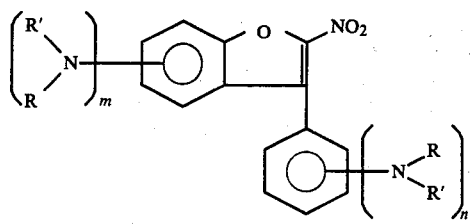

wherein m and n are zero or one and the sum of m and n is one,

R is hydrogen or lower alkyl,

R' is R,

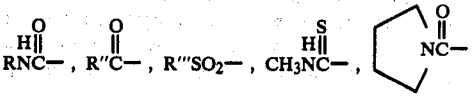

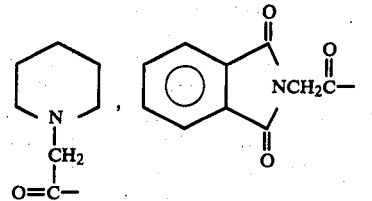

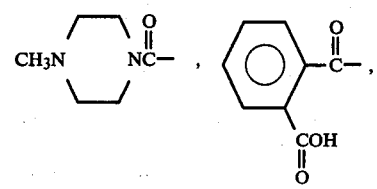

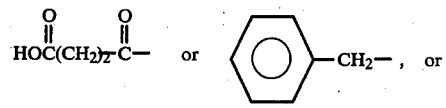

R and R' together form $(CH_3)_2N-N=$,

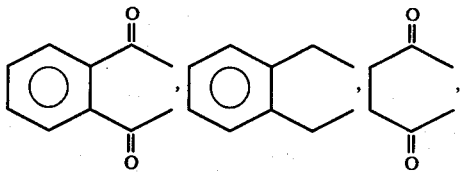

or complete a pyrrole or pyrrolidine ring through the nitrogen atom to which they are bonded, R" is R, lower alkoxy, $CF_3-$ or $ClCH_2-$ and R''' is lower alkyl or $CF_3-$, and pharmaceutically acceptable salts thereof.

The term lower used in connection with alkyl and alkoxy groups herein refers to groups containing from one to four carbon atoms.

The compounds of the invention wherein R is hydrogen are presently preferred. Those compounds in which m is one are also preferred. The more specific preferred classes of the compounds are those in which R is hydrogen and R' is alkyl, in which R is hydrogen and R' is bonded to the nitrogen through a carbonyl group, in which R is hydrogen and R' is bonded to the nitrogen through a sulfonyl group and in which R and R' together with the nitrogen atom to which they are bonded form a cyclic group.

The invention also includes the antimicrobial use of the compounds of the invention.

The compounds of the invention are generally yellowish or orange to red or brown solids when purified. They are generally substantially insoluble in water or aliphatic hydrocarbons and are more soluble in lower alcohols, halogenated solvents, acetone, N,N-dimethylformamide, and the like and, in some cases, dilute mineral acids.

All of the compounds of the invention are active against bacteria and some are also active against other microorganisms including fungi and protozoa, in vitro and topically. Thus, they can be used for disinfecting and sterilizing, for example of medical and dental equipment, as components of disinfecting solutions. The compounds are particularly useful as antibacterial agents. Some of the compounds are also active in vivo in animals. Some of the compounds are active orally. For applications in which water solubility is of importance, the salts are ordinarily used.

The compounds of the invention (I) are prepared by several methods, frequently involving several steps. Ordinarily the individual reactions in these preparative methods are generically known to the art. Furthermore, as will be seen, certain of the compounds (I) are prepared by further reaction of others of the compounds (I) or from corresponding novel azide and isocyanate intermediates (II and III, infra) which are the subject of a commonly assigned application of Vernon R. Fletcher filed of even date herewith, Ser. No. 973,152.

Thus, the compounds of formula I in which R and R' are hydrogen can be obtained by displacement of an aromatic halogen such as bromine from a 3-phenylbenzofuran with, for example, potassium phthalimide in the presence of cuprous iodide by heating in a highly polar solvent such as N,N-dimethylacetamide. The resulting phthalimido-substituted 3-phenylbenzofuran is then nitrated in the 2-position of the benzofuran moiety to provide the compound of the invention wherein R and R' together form a phthalimide group, and the phthalimide group can be cleaved by heating with hydrazine in a suitable non-reactive solvent such as ethanol to provide the amino-substituted 3-phenylbenzofuran. It is generally preferred to form the phthalimido derivative before nitrating in the 2-position and to cleave the phthalimido group after nitrating in the 2-position. Another method for preparing amino-substituted 3-phenylbenzofurans of formula I is by reduction of a corresponding aromatic nitro group, e.g. utilizing stannous chloride in acidic solution (such reaction being carried out before nitrating the 3-phenylbenzofuran moiety in the 2-position). The aromatic amino-substituted-3-phenylbenzofurans can also be prepared from the corresponding carboxylic-substituted compounds by means of a Curtius reaction (e.g. as shown in Example 1).

The primary and secondary amino-substituted-3-phenylbenzofurans of formula I are, in turn, very useful intermediates for preparing other compounds of the invention. They can be reacted with acyl halides, acyl anhydrides, sulfonyl halides, sulfonic anhydrides, formic acid, alkyl chloroformates, imides, metal and alkyl isocyanates and alkyl thioisocyanates with or without inert solvents in generically known methods using conventional techniques as exemplified herein to provide various of the other compounds of the invention.

The ureido-substituted-2-nitro-3-phenylbenzofurans of the invention may be prepared by reaction of the corresponding isocyanates

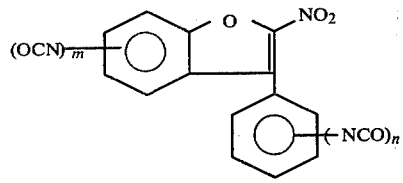

wherein m and n are as previously defined, with primary and secondary amines, and the carbamoyl-substituted compounds (I) are prepared by reaction of the isocyanates (II) with alcohols. The isocyanate intermediates are, in turn, prepared by pyrolysis of the corresponding azides

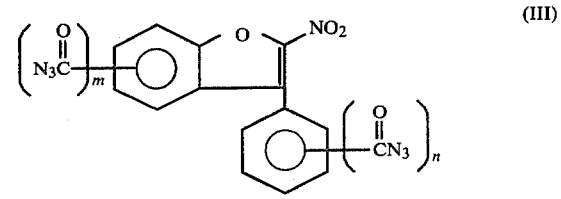

m and n again being as previously defined.

The azides (III) are prepared from 2-nitro-3-phenylbenzofurancarboxylic acids or (2-nitro-3-phenylbenzofuranyl)benzoic acids (described in U.S. Pat. Nos. 4,048,323 and 4,067,993) by reaction with thionyl chloride to provide the carboxyl chlorides followed by reaction with sodium azide to provide the corresponding azides. The azides are then readily pyrolyzed in an inert solvent such as toluene to provide the isocyanates (II) as exemplified in Example 1, Steps A and B).

The acylamido-substituted-2-nitro-3-phenylbenzofurans and alkyl carbamoyl-substituted-2-nitro-3-phenylbenzofurans of the invention are selectively reduced on the acyl group by diborane to provide secondary and tertiary amino-substituted-2-nitro-3-phenylbenzofurans. Thus, the reduction of aromatic, cyclic and acyclic amides (both primary and secondary) is carried out in the presence of an inert solvent, generally tetrahydrofuran.

The pyrrolo-2-nitro-3-phenylbenzofurans are prepared from the amino-2-nitro-3-phenylbenzofurans of the invention by heating the latter with 2,5-dimethoxytetrahydrofuran in the presence of acetic acid or other acid catalysts.

The α-phthalimidoacetamido-2-nitro-3-phenylbenzofurans are prepared from the α-chloroacetamido-2-nitro-3-phenylbenzofurans of the invention by heating the latter with potassium phthalimide in a highly polar solvent such as an N,N-dialkyl alkanamide (e.g. N,N-dimethylformamide, N,N-dimethylacetamide and the like. The α-chloro group may also be readily displaced by refluxing with an amine.

The phthalamido-substituted compounds of the invention are prepared by partially cleaving the phthalimido-substituted-2-nitro-3-phenylbenzofurans of the invention (e.g. as described in Example 29). This reaction is an intermediate step in the preparation of an unsubstituted amino-2-nitro-3-phenylbenzofuran, as described previously.

The compounds of the invention wherein R with R' is =N—N(lower alkyl)$_2$, particularly =N—N(CH$_3$)$_2$, are prepared from the amino-substituted-2-nitro-3-phenylbenzofurans by diazotizing the latter and reacting the resulting diazonium compounds with secondary amines.

The pharmaceutically acceptable salts of the invention are readily prepared by reaction of the corresponding free base with the appropriate hydrogen halide or alkyl halide, optionally in a suitable solvent and evaporation to dryness. Other salts which are not pharmaceutically acceptable may be useful for the synthesis of the basic compounds of the invention or other, acceptable salts or other useful intermediates.

The antimicrobial activity of the compounds is evaluated using a variation of the original agar-plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichia coli,* Streptococcus sp. (strains isolated from dental caries in rats or hamsters at the National Institute of Dental Health and grown in PFY or APT agar), *Asperigillus niger, Candida albicans, Mima polymorpha, Herella vaginicola, Klebsiella pneumoniae* and *Streptococucs fecaelis.*

These are selected representatives of various bacterial and fungal classes and broad spectrum activity can be predicted as a result of activity against them. All of the compounds of the invention possess antimicrobial activity towards one or more of them. The compounds maintain high activity against the microorganisms either in the absence or presence of ten percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intraperitoneally with the test culture. Treatment consists of three oral injections, 1, 6 and 24 hours after infection. All mice are observed for extended periods, e.g. for two weeks, and deaths recorded at daily intervals. Control groups consist of one infected, non-treated group and other infected groups receiving varying dosages of the reference standard.

The acute oral toxicity of the compounds of the invention generally is moderate to low compared with the effective oral dose, and they have a good to excellent therapeutic ratio.

The presently preferred individual compounds of the invention (because of their excellent in vitro antibacterial activity versus Streptococcus sp. and *Escherichia coli*) are:
7-(methyl carbamoyl)-2-nitro-3-phenylbenzofuran,
7-amino-2-nitro-3-phenylbenzofuran,
7-acetamido-2-nitro-3-phenylbenzofuran,
5-amino-2-nitro-3-phenylbenzofuran,
5-acetamido-2-nitro-3-phenylbenzofuran,
5-formamido-2-nitro-3-phenylbenzofuran, ,
5-(ethyl carbamoyl)-2-nitro-3-phenylbenzofuran,
5-methylamino-2-nitro-3-phenylbenzofuran,
2-nitro-3-phenyl-5-ureidobenzofuran,
6-acetamido-2-nitro-3-phenylbenzofuran,
5-methylureido-2-nitro-3-phenylbenzofuran,
5-(α-chloroacetamido)-2-nitro-3-phenylbenzofuran,
2-nitro-3-phenyl-5-trifluoroacetamidobenzofuran and
2-nitro-3-phenyl-5-(n-propyl)ureidobenzofuran.

The compounds of the invention may be formulated by incorporating them into a conventional pharmaceutical carrier material, either organic or inorganic, which is suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for, e.g. oral treatment of a microbial infection, will be an effective amount less than a toxic amount. The amount to be administered to a subject and route of administration to control an infection will depend on the species of organism, the sex, weight, physical condition of the subject, the locus of the infection, and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids or antibacterial agents, or to combine more than one compound described herein in a single formulation.

Certain of the compounds are also active antiparasitics as shown by activity in laboratory tests versus the protozoan Trichomonas sp. In view of the outstanding antimicrobial activity of the compounds, they would also be expected to be effective growth promoters in various animal and bird species.

The following examples are given for the purpose of illustrating the invention, but are in no way limiting thereof. The melting points are uncorrected and are in degrees Centigrade.

EXAMPLE 1

Step A

A sample of 2-nitro-3-phenylbenzofuran-7-carboxylic acid is reacted with thionyl chloride to provide 2-nitro-3-phenylbenzofuran-7-carboxyl chloride. A solution of 9 g. (0.0298 mole) of the chloride in 270 ml. of acetone is treated with 4.5 g. (0.069 mole) of sodium azide dissolved in 15 ml. of water. The mixture is stirred at 20° C. for 3 hours, then poured into 600 ml. of water. The resulting yellow precipitate is separated by filtration, washed with water and dried. This product, the azide intermediate, melts with decomposition at 133° C.

Step B

A mixture of 9.5 g. of the azide product from Step A with 175 ml. of toluene is slowly heated to 100°–110° C. whereupon a gas evolution occurs. At the end of the gas evolution, the mixture is heated and maintained at reflux for 15 minutes. The solvent is then removed by evaporation to provide a yellow solid residue of 2-nitro-3-phenylbenzofuran-7-isocyanate.

Step C

The isocyanate from Step B is dissolved in 100 ml. of glyme and to this solution is added 30 ml. of concentrated hydrochloric acid previously saturated with hydrogen chloride gas. The mixture is stirred and heated to about 70°–80° C., gas evolution occurs and, after this ends, the reaction mixture is allowed to cool gradually to about 20° C. Upon cooling, some solid separates, but the reaction mixture is neutralized with sodium carbonate. The resulting solution is extracted with diethyl ether, the ether solution is washed with water, then dried and the ether is evaporated. The resulting orange solid is recrystallized from aqueous ethanol to provide 7-amino-2-nitro-3-phenylbenzofuran, m.p. 164°–166° C.

| Analysis: | %C | %H | %N |
|---|---|---|---|
| Calculated for $C_{14}H_{10}N_2O_3$: | 66.1; | 3.96; | 11.0 |
| Found: | 66.4; | 3.8; | 10.9. |

EXAMPLE 2

Step A

A mixture of 2.73 g. (0.010 mole) of 5-bromo-3-phenylbenzofuran, 1.9 g. (0.010 mole) of potassium phthalimide and 1.9 g. (0.010 mole) of cuprous iodide in 100 ml. of N,N-dimethylacetamide is flushed with nitrogen gas and heated to its reflux temperature. The mixture is refluxed for 18 hours under a nitrogen atmosphere, allowed to cool to about 20° C. and 150 ml. of 2 N hydrochloric acid is added. The resulting precipitate is separated by filtration and washed with water. The solid is extracted with chloroform, and the extracts are evaporated to provide light yellow crystals of 3-phenyl-5-(N-phthalimido)benzofuran, m.p. 209°–211° C.

| Analysis: | %C | %H | %N |
|---|---|---|---|
| Calculated for $C_{22}H_{13}NO_3$: | 77.9; | 3.9; | 4.1 |
| Found: | 77.4; | 3.9; | 4.0. |

Step B

To a solution of 1.5 g. (0.0044 mole) of the product of Step A in 100 ml. of chloroform is added 2 g. of dinitrogen tetraoxide. The mixture is stirred at about 20° C. for about 18 hours then evaporated to provide a residue which is recrystallized from acetic acid. The product is yellow crystals of 2-nitro-3-phenyl-5-(N-phthalimido)-benzofuran, m.p. 250°–253° C., having the structure

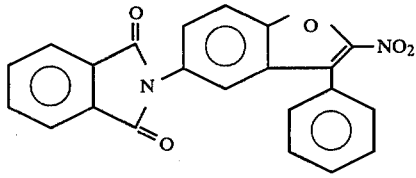

| Analysis: | %C | %H | %N |
|---|---|---|---|
| Calculated for $C_{22}H_{12}N_2O_5$: | 68.7; | 3.1; | 7.3 |
| Found: | 68.0; | 3.2; | 7.1. |

EXAMPLE 3

To a suspension of 1.0 g. of 2-nitro-3-phenyl-5-(N-phthalimido)benzofuran in ethanol is added 0.2 ml. of 64 percent hydrazine. The mixture is refluxed for about 30 minutes and the resulting solution is cooled. The residue which separates is removed by filtration. A large volume of water is added to the remaining solution. Further precipitation occurs to provide orange needles of 5-amino-2-nitro-3-phenylbenzofuran, m.p. 125°–127° C.

| Analysis: | %C | %H | %N |
|---|---|---|---|
| Calculated for $C_{14}H_{10}N_2O_3$: | 66.1; | 4.0; | 11.0 |

-continued

| Analysis: | %C | %H | %N |
|---|---|---|---|
| Found: | 66.1; | 3.9; | 11.1. |

EXAMPLE 4

Step A

Using the method of Example 2, Step A, the compound 6-bromo-3-phenylbenzofuran is reacted with potassium phthalimide in the presence of cuprous iodide to provide 3-phenyl-6-(N-phthalimido)benzofuran.

Step B

To a 10 g. sample of the product of Step A in 900 ml. of warm acetonitrile is added 3 g. of dinitrogen tetraoxide. The mixture is stirred at 60° C. for 5 minutes, then allowed to stir at about 20° C. for about 3 hours. The solution is flushed with nitrogen gas, then evaporated to provide a residue. The residue is suspended in and mixed thoroughly with ethanol, and the yellow solid is separated by filtration. The product is 2-nitro-3-phenyl-6-(N-phthalimido)benzofuran which is recrystallized from chloroform to provide yellow crystals, m.p. 246°–248° C. (dec.).

EXAMPLE 5

Using the method of Example 3, 2-nitro-3-phenyl-6-(N-phthalimido)benzofuran is reacted with hydrazine to provide red crystals of 6-amino-2-nitro-3-phenylbenzofuran, m.p. 212°–214° C.

| Analysis: | %C | %H | %N |
|---|---|---|---|
| Calculated for $C_{14}H_{10}N_2O_3$: | 66.1; | 4.0; | 11.0 |
| Found: | 65.7; | 3.9; | 11.0. |

EXAMPLE 6

A mixture of 2 g. of 5-amino-3-phenylbenzofuran and 2 g. of succinic anhydride in 25 ml. of acetic acid is heated to its reflux temperature and maintained at reflux for 2 hours. The mixture is cooled, then filtered to remove 5-(β-carboxypropionamido)-2-nitro-3-phenylbenzofuran (see Example 30 hereof).

The filtrate is heated on a steam bath and water is added until some precipitate begins to form. The solution is then cooled to provide yellow crystals of 2-nitro-3-phenyl-5-(N-succinimido)benzofuran, m.p. 213° C. (dec.) having the structure

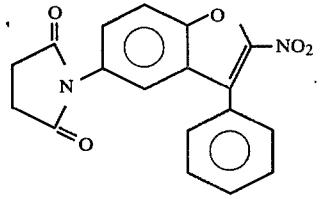

| Analysis: | % C | % H | % N |
|---|---|---|---|
| Calculated for $C_{18}H_{12}N_2O_5 \cdot \frac{1}{4} H_2O$: | 63.4; | 3.7; | 8.2 |
| Found: | 63.2; | 3.7; | 8.3. |

EXAMPLE 7

To a suspension of 2.3 g. (0.0068 mole) of 2-nitro-3-phenyl-5-(n-succinimido)benzofuran in 50 ml. of tetrahydrofuran is added 20 ml. of 1-N diborane in tetrahydrofuran and the mixture is stirred at room temperature for 20 hours under a nitrogen atmosphere. The solution is treated with 20 ml. of 6 N hydrochloric acid, refluxed for 45 minutes and evaporated to provide a residue which is partitioned between saturated sodium bicarbonate solution and chloroform. The chloroform layer is dried, then evaporated to provide a dark red residue. The residue is recrystallized from a mixture of N,N-dimethylformamide and water to provide 2-nitro-3-phenyl-5-(N-pyrrolidino)benzofuran, m.p. 189°–193° C. having the structure

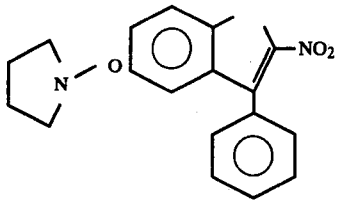

| Analysis: | %C | % H | % N |
|---|---|---|---|
| Calculated for $C_{18}H_{16}N_2O_3$: | 70.1; | 4.6; | 7.7 |
| Found: | 70.2; | 5.3; | 9.1. |

EXAMPLE 8

Using the method of Example 7, 2-nitro-3-phenyl-5-(N-phthalimido)benzofuran is reduced with diborane to provide 5-(N-isoindolinyl)-2-nitro-3-phenylbenzofuran, m.p. 228°–230° C., having the structure

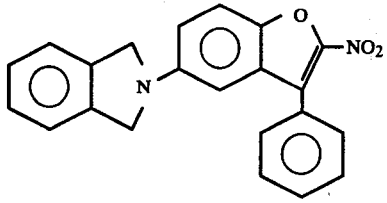

| Analysis: | % C | % H | % N |
|---|---|---|---|
| Calculated for $C_{22}H_{16}N_2O_3 \cdot \frac{1}{4} H_2O$: | 72.3; | 4.6; | 7.7 |
| Found: | 72.1; | 4.2; | 7.7. |

EXAMPLE 9

To a solution of 0.33 g. of 5-amino-2-nitro-3-phenylbenzofuran in 3 ml. of acetic acid is added 0.33 g. of 2,5-dimethoxytetranydrofuran, and the mixture is heated on a steam bath for about 1 hour. On cooling, a solid crystallizes and is separated by filtration to provide brown needles of 2-nitro-3-phenyl-5-(N-pyrrolo)-benzofuran, m.p. 163°–165° C. having the structure

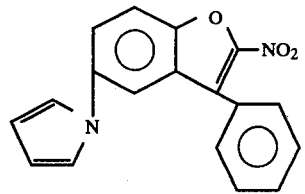

| Analysis: | % C | % H | % N |
|---|---|---|---|
| Calculated for $C_{18}H_{12}N_2O_3$: | 71.0; | 4.0; | 9.2 |
| Found: | 71.0; | 4.0; | 9.1. |

EXAMPLE 10

To a solution of 3 g. of 5-amino-2-nitro-3-phenylbenzofuran in 15 ml. of pyridine is added 3 ml. of propionyl chloride at about 20° C. while stirring. A solid precipitates from the reaction mixture upon cooling. The mixture is washed with dilute hydrochloric acid, the product is separated by filtration, then recrystallized from an isopropanol-water mixture. The product is yellow crystals of 2-nitro-3-phenyl-5-propionamidobenzofuran, m.p. 179°–182° C.

| Analysis: | % C | % H | % N |
|---|---|---|---|
| Calculated for $C_{17}H_{14}N_2O_4$: | 65.8; | 4.5; | 9.0 |
| Found: | 65.8; | 4.7; | 9.0. |

EXAMPLE 11

Using the method of Example 10, 5-amino-2-nitro-3-phenylbenzofuran is reacted with α-chloroacetyl chloride in acetic acid to provide 5-(α-chloroacetamido)-2-nitro-3-phenylbenzofuran.

| Analysis: | % C | % H | % N |
|---|---|---|---|
| Calculated for $C_{16}H_{11}CLN_2O_4$: | 58.1; | 3.4; | 8.5 |
| Found: | 57.7; | 3.4; | 8.4. |

EXAMPLE 12

To a 0.33 g. sample of 5-amino-2-nitro-3-phenylbenzofuran is added 1 ml. of acetic anhydride, and the mixture is heated for 5 minutes on a steam bath. About 10 ml. of isopropanol is added, and the mixture is again heated on a steam bath to dissolve the solid. It is then saturated with hot water and cooled to provide yellow needles of 5-acetamido-2-nitro-3-phenylbenzofuran, m.p. 204°–207° C.

| Analysis: | % C | % H | % N |
|---|---|---|---|
| Calculated for $C_{16}H_{12}N_2O_4$: | 64.9; | 4.1; | 9.4 |
| Found: | 65.0; | 4.1; | 9.6. |

EXAMPLE 13

To a sample of 0.33 g. of 5-amino-2-nitro-3-phenylbenzofuran is added 3 ml. of 97 percent formic acid. The mixture is heated on a steam bath for about 45 minutes, saturated with hot water, then cooled to provide a yellow solid. The product is 5-formamido-2-nitro-3-phenylbenzofuran, m.p. 175°–178° C.

| Analysis: | % C | % H | % N |
|---|---|---|---|
| Calculated for $C_{15}H_{10}N_2O_4$: | 63.8; | 3.6; | 9.9 |
| Found: | 63.4; | 3.4; | 10.1. |

EXAMPLE 14

Using the method of Example 12, 7-amino-2-nitro-3-phenylbenzofuran is reacted with acetic anhydride to provide yellow solid 7-acetamido-2-nitro-3-phenylbenzofuran, m.p. 224°–226° C.

EXAMPLE 15

Using the method of Example 12, 6-amino-2-nitro-3-phenylbenzofuran is reacted with acetic anhydride to provide 6-acetamido-2-nitro-3-phenylbenzofuran, m.p. 212°–214° C.

EXAMPLE 16

Using the method of Example 12, 7-amino-2-nitro-3-phenylbenzofuran is reacted with trifluoroacetic anhydride in dichloromethane to provide 7-trifluoroacetamido-2-nitro-3-phenylbenzofuran, m.p. 194.5°–196° C.

EXAMPLE 17

Step A

To a solution of 0.75 g. of 5-amino-2-nitro-3-phenylbenzofuran in 5 ml. of pyridine is added 1 ml. of benzoyl chloride. The mixture is heated on a steam bath for about 1 hour, then decanted into 50 ml. of 2 N hydrochloric acid. A yellow residue forms which is recrystallized from a mixture of isopropanol, methanol and water to provide yellow crystals of 5-benzamido-2-nitro-3-phenylbenzofuran having the structure

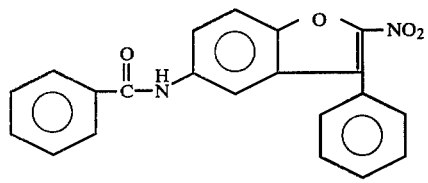

Step B

The product of Step A is dissolved in 50 ml. of tetrahydrofuran and treated with 5 ml. of 1 N diborane in tetrahydrofuran at about 20° C. over a period of about 16 hours. The mixture is treated with 5 ml. of 6 N hydrochloric acid and heated on a steam bath for about ½ hour. 20 ml. of saturated sodium bicarbonate solution is added, the mixture is extracted with chloroform and the extracts are dried, then evaporated to provide a residue. The residue is recrystallized from a mixture of isopropanol and water to yield red needles of 5-benzylamino-2-nitro-3-phenylbenzofuran, m.p. 118°–120° C. having the structure

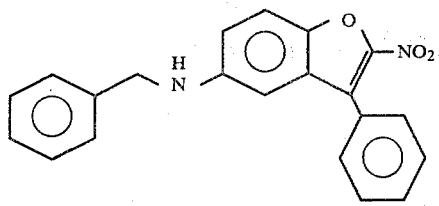

| Analysis: | % C | % H | % N |
|---|---|---|---|
| Calculated for $C_{21}H_{16}N_2O_3$: | 73.2; | 4.7; | 8.1 |
| Found: | 73.4; | 4.7; | 8.1. |

EXAMPLE 18

To a solution of 1.8 g. of 2-nitro-3-phenyl-5-propionamidobenzofuran in 50 ml. of tetrahydrofuran is added 10 ml. of 1 N diborane, and the solution is stirred for about 18 hours under a nitrogen atmosphere. To this mixture is cautiously added 5 ml. of 6 N hydrochloric acid. The mixture is heated to its reflux temperature and maintained at reflux for about 30 minutes. The solution is evaporated to provide a residue which is partitioned between cold sodium bicarbonate solution and chloroform. The chloroform extracts are dried, then evaporated to provide a red residue which is recrystallized from aqueous ethanol to provide red crystals of 2-nitro-3-phenyl-5-(n-propyl)aminobenzofuran, m.p. 158°–160° C.

| Analysis: | % C | % H | % N |
|---|---|---|---|
| Calculated for $C_{17}H_{16}N_2O_3$: | 68.9; | 5.4; | 9.4 |
| Found: | 68.6; | 5.4; | 9.4. |

EXAMPLE 19

To a solution of 1.5 g. of 5-amino-2-nitro-3-phenylbenzofuran in 10 ml. of pyridine at 0° C. are added 2 ml. of ethyl chloroformate. The mixture is stirred at about 20° C. for about 10 minutes, then diluted with cold 3 N hydrochloric acid. The solid product is separated by filtration, washed with dilute hydrochloric acid and water, then recrystallized from aqueous ethanol. The product is yellow crystals of 5-(ethyl carbamoyl)-2-nitro-3-phenylbenzofuran, m.p. 154°–156° C.

| Analysis: | % C | % H | % N |
|---|---|---|---|
| Calculated for $C_{17}H_{14}N_2O_5$: | 62.6; | 4.3; | 8.6 |
| Found: | 62.4; | 4.3; | 8.7. |

EXAMPLE 20

To a solution of 1.3 g. of 5-(ethyl carbamoyl)-2-nitro-3-phenylbenzofuran in 30 ml. of tetrahydrofuran is added 10 ml. of 1 N diborane. The mixture is heated to its reflux temperature and maintained at reflux for 4 hours. The mixture is cooled, then treated with 5 ml. of 6 N hydrochloric acid. This solution is heated and maintained at reflux for about 30 minutes, then evaporated, and the residue is partitioned between saturated sodium bicarbonate solution and chloroform. The chloroform solution is washed with saturated sodium chloride solution, then dried. The dried solution is evaporated to provide a residue which is recrystallized from isopropanol. The product is red crystals of 5-methylamino-2-nitro-3-phenylbenzofuran, m.p. 156°–159° C.

| Analysis: | % C | % H | % N |
|---|---|---|---|
| Calculated for $C_{15}H_{12}N_2O_3$: | 67.2; | 4.5; | 10.4 |
| Found: | 66.7; | 4.5; | 10.3. |

EXAMPLE 21

A mixture of 0.9 g. of 5-(n-propyl)amino-2-nitro-3-phenylbenzofuran in 3 ml. of acetic anhydride is heated on a steam bath for about 30 minutes. The mixture is added to methanol to provide a solution which is saturated while hot with water. On cooling, yellow crystals of 2-nitro-3-phenyl-5-[N-(n-propyl)acetamido]benzofuran form, m.p. 130°–134° C.

| Analysis: | % C | % H | % N |
|---|---|---|---|
| Calculated for $C_{19}H_{18}N_2O_4$: | 67.4; | 5.4; | 8.3 |
| Found: | 67.8; | 5.3; | 8.3. |

EXAMPLE 22

A sample of 2-nitro-3-phenyl-5-[N-(n-propyl)acetamido]benzofuran is reduced in tetrahydrofuran with 1 N diborane to provide 3-[N-ethyl-N-(n-propyl)amino]-2-nitro-3-phenylbenzofuran, m.p. 99°–100° C.

| Analysis: | % C | % H | % N |
|---|---|---|---|
| Calculated for $C_{19}H_{20}N_2O_2$: | 70.3; | 6.2; | 8.6 |
| Found: | 69.9; | 6.3; | 8.6. |

EXAMPLE 23

To a solution of 2-nitro-3-phenylbenzofuran-7-isocyanate in toluene is added a large excess of methanol. The solution is stirred for about 15 minutes, then evaporated to provide a yellow crystalline residue which is recrystallized from ethanol to provide yellow needles of 7-(methyl carbamoyl)-2-nitro-3-phenylbenzofuran, m.p. 167°–169° C.

| Analysis: | % C | % H | % N |
|---|---|---|---|
| Calculated for $C_{16}H_{12}N_2O_5$: | 61.5; | 3.9; | 9.0 |
| Found: | 61.0; | 4.0; | 9.0. |

EXAMPLE 24

A solution of 2-nitro-3-phenylbenzofuran-7-isocyanate is prepared from 3.5 g. of the corresponding azide by heating in 25 ml. of toluene at a bath temperature of 105° C., then refluxing for 10 minutes. To ⅓ of this isocyanate solution is added 20 ml. of pyrrolidine. After 1 hour of stirring, the solvent is removed by evaporation to provide a yellow residue which is recrystallized from methanol to provide 1,1-tetramethylene-3-[7-(2-nitro-3-phenylbenzofuranyl)]urea, m.p. 215°–216° C., having the structure

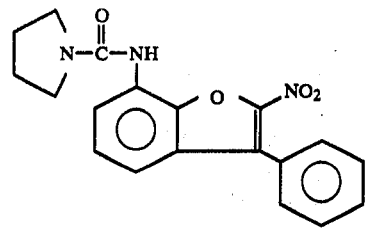

| Analysis: | % C | % H | % N |
|---|---|---|---|
| Calculated for $C_{19}H_{17}N_3O_4$: | 65.0; | 4.9; | 12.0 |
| Found: | 64.9; | 4.8; | 11.9. |

EXAMPLE 25

To a 25 ml. portion of the solution of 2-nitro-3-phenylbenzofuran-7-isocyanate from Example 24 is added 2 ml. of n-butylamine. The mixture is stirred for 1 hour, then evaporated to provide a residue which is recrystallized from aqueous methanol. The product is 1-(n-butyl)-3-[7-(2-nitro-3-phenylbenzofuranyl]urea, m.p. 194°–196.5° C. having the structure

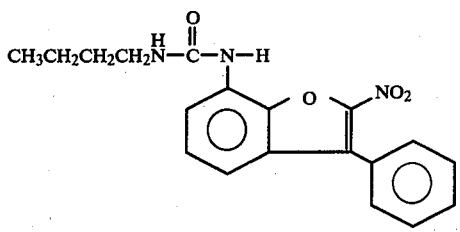

| Analysis: | % C | % H | % N |
|---|---|---|---|
| Calculated for $C_{19}H_{19}N_3O_4$: | 64.6; | 5.4; | 11.9 |
| Found: | 64.6; | 5.2; | 11.7. |

EXAMPLE 26

To the remaining ⅓ of the solution from Example 24 which consists of 25 ml. of a toluene solution of 2-nitro-3-phenylbenzofuran-7-isocyanate is added 2 ml. of N-methylpiperazine. After stirring for 1 hour the reaction mixture is evaporated to provide a residue which gradually solidifies. The crude material is recrystallized to provide yellow crystals of 1,1-[3-(N-methyl)azapentamethylene]-3-[2-nitro-3-phenylbenzofuranyl]urea, m.p. 162°–163° C., having the structure

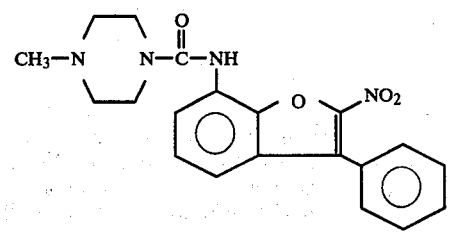

| Analysis: | % C | % H | % N |
|---|---|---|---|
| Calculated for $C_{20}H_{20}N_4O_4$: | 63.2; | 5.3; | 14.7 |
| Found: | 63.0; | 5.2; | 14.6. |

EXAMPLE 27

To a solution of 1 g. (0.0039 mole) of 5-amino-2-nitro-3-phenylbenzofuran in 50 ml. of warm benzene is added 2 ml. of methyl thioisocyanate. The mixture is heated to its reflux temperature and maintained at reflux for two hours, then cooled and filtered. The filtrate is evaporated to provide a residue which is recrystallized from aqueous isopropanol to provide orange crystals of 5-methyl-thioureido-2-nitro-3-phenylbenzofuran, m.p. 180°–181° C., having the structure

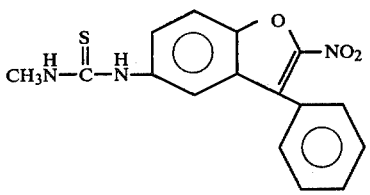

| Analysis: | % C | % H | % N |
|---|---|---|---|
| Calculated for $C_{16}H_{13}N_3O_3S$: | 58.7; | 4.0; | 12.8 |
| Found: | 58.9; | 4.0; | 12.7. |

EXAMPLE 28

To a mixture of 1 g. (0.0039 mole) of 5-amino-2-nitro-3-phenylbenzofuran in 25 ml. of benzene is added 2 ml. of methyl isocyanate, and the mixture is heated on a steam bath for 20 minutes, then cooled. The solid precipitate which forms is separated by filtration, then recrystallized from a mixture of N,N-dimethylformamide and water. The product is orange needles of 5-methylureido-2-nitro-3-phenylbenzofuran, m.p. 243°–247° C. (dec.), having the structure

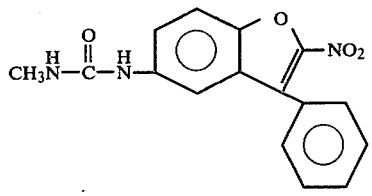

| Analysis: | % C | % H | % N |
|---|---|---|---|
| Calculated for $C_{16}H_{13}N_3O_4$: | 61.7; | 4.2; | 13.5 |
| Found: | 61.8; | 4.1; | 13.6. |

EXAMPLE 29

A mixture of 5 g. of 2-nitro-3-phenyl-5-(N-phthalimido)benzofuran, 100 ml. of methanol, 50 ml. of 10 percent sodium hydroxide solution and 250 ml. of water is heated on a steam bath for 15 minutes. The mixture is filtered, then the filtrate is acidified with 6N hydrochloric acid. The resulting precipitate is separated by filtration, then recrystallized from isopropanol to provide yellow crystals of 2-nitro-3-phenyl-5-phthalamidobenzofuran, m.p. 247°–252° C., having the structure

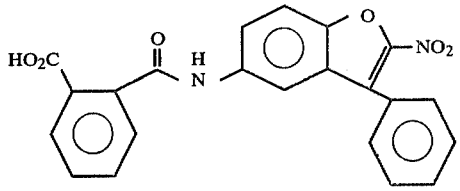

| Analysis: | % C | % H | % N |
|---|---|---|---|
| Calculated for $C_{22}H_{14}N_2O_6$: | 65.7; | 3.5; | 7.0 |
| Found: | 66.0; | 3.6; | 6.8. |

EXAMPLE 30

A mixture of 2 g. of 5-amino-2-nitro-3-phenylbenzofuran and 2 g. of succinic anhydride in 25 ml. of acetic acid is heated to its reflux temperature and maintained at reflux for 2 hours. The solution is cooled, and the precipitate obtained is separated by filtration. The product is yellow crystals of 5-($\beta$-carboxypropionamido)-2-nitro-3-phenylbenzofuran, m.p. 223°–225° C.

| Analysis: | % C | % H | % N |
|---|---|---|---|
| Calculated for $C_{18}H_{14}N_2O_6$: | 61.0; | 4.0; | 7.9 |
| Found: | 60.7; | 4.0; | 7.8. |

EXAMPLE 31

To a solution of 0.62 g. (0.00244 mole) of 7-amino-2-nitro-3-phenylbenzofuran in 10 ml. of pyridine is added with stirring 0.3 g. of methanesulfonyl chloride. The reaction is stirred at about 20° C. for about 16 hours, then poured into ice water acidified with hydrochloric acid. This solution is extracted with a mixture of diethyl ether and dichloromethane and the extracts are washed twice with water and then dried. The dried extracts are evaporated to provide a residue which is recrystallized twice from benzene with decolorizing charcoal to provide yellow solid 7-methanesulfonamido-2-nitro-3-phenylbenzofuran, m.p. 169°–171.5° C.

| Analysis: | % C | % H | % N |
|---|---|---|---|
| Calculated for $C_{15}H_{12}N_2O_5S$: | 54.2; | 3.6; | 8.4 |
| Found: | 54.3; | 3.7; | 8.5. |

EXAMPLE 32

Step A 60 g. of 3-nitroacetophenone in 250 ml. of chloroform is treated with 58.2 g. of bromine in 50 ml. of chloroform. The solvent is evaporated and the product separated by filtration and recrystallized from benzene to provide α-bromo-3-nitroacetophenone, m.p. 91°–94° C.

Step B

A mixture of 0.36 mole of α-bromo-3-nitroacetophenone, 0.36 mole of phenol, 0.36 mole of potassium carbonate and 1 g. of sodium iodide in 250 ml. of benzene is heated at reflux for 7 hours. Water is removed using a Dean-Stark trap. The reaction mixture is then diluted with water and diethyl ether, filtered and the filtrate is separated into aqueous and organic layers. The organic layer is washed with dilute sodium hydroxide solution, sodium chloride solution and dried. The solvent is evaporated to provide a residue which is suspended in a mixture of benzene and hexane. After standing for several hours, a solid is collected which is recrystallized from a benzene-hexane mixture to provide α-phenoxy-3-nitroacetophenone, m.p. 116°–118° C.

Step C

A mixture of 29.5 g. of the product from Step B and 400 g. of polyphosphoric acid is heated at 60° C. for about 16 hours, then poured into water. This solution is extracted with a mixture of benzene and ether. The extracts are dried, then evaporated to provide a residue which is extracted with hot cyclohexane. Upon cooling, a yellow solid forms and this is recrystallized from isopropanol to provide 3-(3-nitrophenyl)benzofuran, m.p. 86°–86.5° C.

| Analysis: | % C | % H | % N |
|---|---|---|---|
| Calculated for $C_{14}H_9NO_3$: | 70.3; | 3.8; | 5.9 |
| Found: | 70.0; | 3.7; | 5.8. |

Step D

A solution of stannous chloride (107 ml. of 2.0 M solution in acetic acid) and 10 g. of 3-(3-nitrophenyl)benzofuran is stirred at 20° C. for about 72 hours. The solution is diluted with water and basified with 50 percent sodium hydroxide solution. The aqueous solution is then extracted with dichloromethane. The dichloromethane solution is washed with water, then dried and finally evaporated to provide a residue. Infrared spectral analysis of the product shows that it is 3-(3-aminophenyl)benzofuran. This product readily form a hydrochloride salt, m.p. 218°–219° C.

Step E

A mixture of 7 g. of the product of Step D in 100 ml. of chloroform is treated dropwise with 10 g. of trifluoromethanesulfonic anhydride. This mixture is cooled with an ice bath, and to it is added 4.4 g. of N,N-dimethylaniline. The mixture is slowly warmed (to about 50° C. for 1 hour) then allowed to cool to about 20° C. and stand overnight. The reaction mixture is evaporated, and the residue is diluted with diethyl ether and water and acidified with hydrochloric acid. The aqueous acidic layer is separated, and the organic layer is washed with sodium chloride solution. The organic layer is then extracted with dilute sodium hydroxide solution. The aqueous basic solution is then poured into cold dilute hydrochloric acid to precipitate a solid. The solid residue is separated and extracted into diethyl ether. The ether solution is washed with sodium chloride solution, then dried. The solution is evaporated to provide an oil which gradually solidifies. The oil is dissolved in chloroform and eluted through a column of silica gel with chloroform. The solid obtained in the early fractions is crystallised from cyclohexane to provide 3-(3-benzofuranyl)trifluoromethanesulfonanilide, m.p. 88.5°–89.5° C.

| Analysis: | % C | % H | % N |
|---|---|---|---|
| Calculated for $C_{15}H_{10}F_3NO_3S$: | 52.8; | 2.5; | 4.1 |
| Found: | 52.8; | 2.6; | 4.1. |

Step F

To a solution of 5.5 g. of the product of Step E in 100 ml. of chloroform is added 2.58 g. of bromine dissolved in 10 ml. of chloroform. After stirring for about 1 hour, the solution is evaporated to provide a residue. The residue is determined to be 3-(2-bromo-3-benzofuranyl)trifluoromethanesulfonanilide by infrared spectral analysis.

Step G.

A mixture of 6.7 g. of the product of Step F, 1.5 g. of dinitrogen tetraoxide and 1.4 g. of cyclohexene in acetic acid is stirred at 20° C. for about 16 hours. The mixture is filtered, then evaporated to provide a residue which is chromatographed on silica gel, eluting with chloroform, to provide a number of fractions which are examined by infrared spectral analysis. The middle fractions are eluted with a mixture of 90 percent chloroform and 10 percent methanol. These middle fractions are evaporated to provide a residue which is treated with a solution of triethylamine and isopropyl ether. The solid product from this reaction is recrystallized from a mixture of isopropanol and isopropyl ether. The product is 3-(2-nitro-3-benzofuranyl)trifluoromethanesulfonanilide triethylamine salt, m.p. 101°–102.5° C.

| Analysis: | % C | % H | % N |
|---|---|---|---|
| Calculated for $C_{15}H_8F_3N_2O_5S.C_6H_{15}N$: | 51.8; | 4.8; | 8.6 |
| Found: | 51.9; | 5.0; | 8.8. |

EXAMPLE 33

Using the method of Example 32, Step E, 7-amino-2-nitro-3-phenylbenzofuran is reacted with trifluoromethanesulfonic anhydride to provide 2-nitro-3-phenyl-7-trifluoromethanesulfonamidobenzofuran. This product is purified by chromatography on silica gel eluting with chloroform. The first fraction provides the desired product which is further purified by recrystallization from benzene to provide yellow-orange crystals, m.p. 168°–170.5° C.

| Analysis: | % C | % H | % N |
|---|---|---|---|
| Calculated for $C_{15}H_9F_3N_2O_5S$: | 46.7; | 2.4; | 7.3 |
| Found: | 46.9; | 2.4; | 7.1. |

EXAMPLE 34

Using the method of Example 33, 6-amino-2-nitro-3-phenylbenzofuran is reacted to provide 2-nitro-3-phenyl-6-trifluoromethanesulfonamidobenzofuran as the triethylamine salt. This product is obtained by purifying the reaction product by chromatography on silica gel followed by reaction of the sulfonanilide with triethylamine to provide the salt product, m.p. 114°–120° C.

| Analysis: | % C | % H | % N |
|---|---|---|---|
| Calculated for $C_{15}H_9F_3N_2O_5S.C_6H_{15}N$: | 51.8; | 4.8; | 8.6 |
| Found: | 51.8; | 5.0; | 8.6. |

EXAMPLE 35

To a solution of 0.75 g. of 5-amino-2-nitro-3-phenylbenzofuran in 5 ml. of glacial acetic acid and 3 ml. of water is added an equimolar amount of potassium isocyanate dissolved in 5 ml. of warm water. The reaction is stirred at about 20° C. for 30 minutes then filtered to separate the solid product. The solid is recrystallized from aqueous methanol to provide yellow crystals of 2-nitro-3-phenyl-5-ureidobenzofuran, m.p. 230°-232° C.

| Analysis: | % C | % H | % N |
|---|---|---|---|
| Calculated for $C_{15}H_{11}N_3O_4$: | 60.6; | 3.7; | 14.1 |
| Found: | 60.4; | 3.7; | 14.5. |

EXAMPLE 36

To a suspension of 5-amino-2-nitro-3-phenylbenzofuran in 200 ml. of water and 3 ml. of 12 N hydrochloric acid which has been cooled to 0° C. is slowly added, with stirring, 0.8 g. of sodium nitrite mixed into 5 ml. of water. The mixture is stirred for about 10 minutes, then 40 percent aqueous dimethylamine solution is added slowly until the reaction mixture becomes basic. A solid begins to precipitate. The solid is separated by filtration then recrystallized from a mixture of N,N-dimethylformamide in water to provide orange crystals. The product is 5-(3,3-dimethyltriazino)-2-nitro-3-phenylbenzofuran, m.p. 202° C. (dec.) having the structure

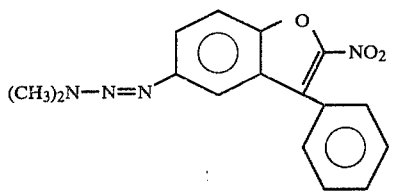

| Analysis: | % C | % H | % N |
|---|---|---|---|
| Calculated for $C_{16}H_{14}N_4O_3$: | 61.9; | 4.5; | 18.0 |
| Found: | 62.2; | 4.5; | 18.1. |

EXAMPLE 37

A mixture of 5 g. of 5-chloroacetamido-2-nitro-3-phenylbenzofuran and 3 g. of potassium phthalimide in 20 ml. of N,N-dimethylformamide is heated to its reflux temperature and maintained at reflux for 40 minutes. To this reaction mixture is added 75 ml. of water. A solid is obtained upon cooling which is recrystallized from aqueous acetic acid to provide brown crystals of 2-nitro-3-phenyl-5-[α-(N-phthalimido)acetamido]benzofuran, m.p. 233°-235° C., having the structure

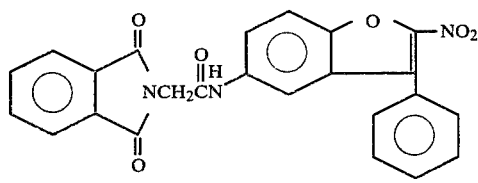

| Analysis: | % C | % H | % N |
|---|---|---|---|
| Calculated for $C_{24}H_{15}N_2O$: | 65.3; | 3.4; | 9.5 |
| Found: | 65.4; | 3.5; | 9.3. |

EXAMPLE 38

A mixture of 2 g. of 5-amino-2-nitro-3-phenylbenzofuran and 10 ml. of trifluoroacetic anhydride is heated for 20 seconds on a steam bath. Excess trifluoroacetic anhydride is evaporated off to provide a solid which is recrystallized from aqueous methanol. The product is yellow crystals of 2-nitro-3-phenyl-5-trifluoroacetamidobenzofuran, m.p. 153°-156° C.

| Analysis: | % C | % H | % N |
|---|---|---|---|
| Calculated for $C_{16}H_9F_3N_2O_4$: | 54.9; | 2.6; | 8.0 |
| Found: | 55.0; | 2.5; | 8.1. |

EXAMPLE 39

To a solution of 2 g. of 5-amino-2-nitro-3-phenylbenzofuran in 100 ml. of hot benzene is added 4 ml. of n-propyl isocyanate. The mixture is heated on a steam bath for 30 minutes, then evaporated to dryness. The residue is recrystallized from aqueous methanol to provide orange crystals of 2-nitro-3-phenyl-5-(n-propyl)ureidobenzofuran, m.p. 199°-201° C., having the structure

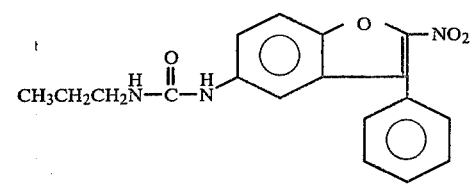

| Analysis: | % C | % H | % N |
|---|---|---|---|
| Calculated for $C_{18}H_{17}N_3O_4$: | 63.7; | 5.0; | 12.4 |
| Found: | 64.0; | 5.1; | 12.7. |

EXAMPLE 40

Step A

A mixture of 40.5 g. (0.43 mole) of phenol, 100 g. (0.428 mole) of 4-chloro-α-bromoacetophenone, 100 g. (0.725 mole) of potassium carbonate and 500 ml. of glyme is heated to its reflux temperature and maintained at reflux for about 6 hours. The reaction mixture is evaporated to remove the solvent. The residue is diluted with water and diethyl ether, and the layers are separated. The ether layer is washed with water and saturated sodium chloride solution and dried over magnesium sulfate. The ether solution is evaporated to provide a dark oil gradually solidifies on cooling. The solid is recrystallized from ethanol to provide 4-chloro-α-phenoxyacetophenone, m.p. 81°-86° C.

Step B

A mixture of 350 g. of polyphosphoric acid and 51.3 g. (0.208 mole) of 4-chloro-α-phenoxyacetophenone is heated to a temperature of about 80° C. and maintained at this temperature for about 1 hour. The reaction mixture is then poured into cold water. The yellow product is collected, washed with water and dissolved in diethyl ether. The ether solution is washed with cold dilute sodium hydroxide solution, water and saturated sodium chloride solution, then dried over sodium sulfate. The solvent is evaporated to provide a dark oil which solidifies to 3-(4-chlorophenyl)benzofuran. The structural assignment is supported by infrared spectral analysis.

Step C

Using the method of Example 4, Step A, and reacting the product of Step B with potassium phthalimide, one obtains 3-[4-phthalimido)phenyl]benzofuran.

Step D

Using the method of Example 4, Step B, the product of Step C is nitrated to provide 2-nitro-3-[4-(N-phthalimido)phenyl]benzofuran, having the structure

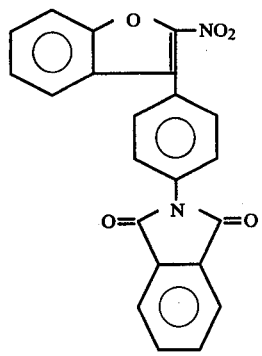

EXAMPLE 41

Using the method of Example 3, 2-nitro-3-[4-(N-phthalimido)phenyl]benzofuran is reacted with hydrazine to provide 3-(4'-aminophenyl)-2-nitrobenzofuran.

EXAMPLE 42

Using the method of Example 10, 3-(4'-aminophenyl)-2-nitrobenzofuran is reacted with propionyl chloride to provide 2-nitro-3-(4-propionamido)phenylbenzofuran.

EXAMPLE 43

Using the method illustrated in Example 22, 2-nitro-3-(4-propionamidophenyl)benzofuran is reduced to provide 2-nitro-3-(4-n-propylaminophenyl)benzofuran.

EXAMPLE 44

Step A

A mixture of 45.2 g. (0.198 mole) of 3-(4-chlorophenyl)benzofuran, 22.2 g. (0.248 mole) of cuprous cyanide and 15 ml. of pyridine is heated to 220° C. and maintained at this temperature for one day. The mixture is then poured into a solution of 47.5 g. of ferric chloride, 30 ml. of concentrated hydrochloric acid and 135 ml. of water with stirring. The mixture is stirred with heating below its boiling point for 1 hour. The aqueous portion is removed, and the organic portion is mixed with 1.2 liter of benzene, and the mixture is stirred for 1 hour. The mixture is then filtered. The filtrate is washed with 6 N hydrochloric acid, water, 10 percent sodium hydroxide solution and saturated sodium chloride solution, then dried over magnesium sulfate. The benzene solution is then evaporated to provide a dark oil which solidifies to provide 3-(4-cyanophenyl)benzofuran. The infrared spectrum of the product is consistent with the assigned structure.

Step B

A mixture of 24.4 g. (0.111 mole) of 3-(4-cyanophenyl)benzofuran, 25 g. of 85 percent potassium hydroxide and 250 ml. of 95 percent aqueous ethanol is heated to its reflux temperature and maintained at reflux for 15 hours. The solvent is removed by evaporation, and the residue is diluted with water and diethyl ether.

The solid precipitate is separated and dissolved in 800 ml. of hot water. This aqueous solution is then acidified with 6 N hydrochloric acid to provide a white precipitate which is collected by filtration and washed with water. The white product is then recrystallized from 1,2-dichloroethane to provide 4-(3-benzofuranyl)benzoic acid, m.p. 222°–225° C.

| Analysis: | % C | % H |
|---|---|---|
| Calculated for C₁₅H₁₁O₃: | 75.6; | 4.24 |
| Found: | 75.6; | 4.10. |

Step C

A stirred solution of 14 g. (0.059 mole) of 3-(3-benzofuranyl)benzoic acid and 1500 ml. of 1,2-dichloroethane which has been heated to its reflux temperature a slowly cooled to about 60° C. is treated dropwise with 9.4 g. (0.059 mole) of bromine diluted with 7 ml. of 1,2-dichloroethane. After stirring the mixture for about 50 hours at about 55° C., the reaction mixture is cooled, and the solid precipitate is collected and rinsed with 1,2-dichloroethane. Infrared spectral analysis of the crude product, 4-(2-bromo-3-benzofuranyl)benzoic acid, is consistent with the assigned structure. The crude product has a melting point of 218°–220° C.

Step D

A mixture of 18.7 g. (0.059 mole) of 4-(2-bromo-3-benzofuranyl)benzoic acid and 1200 ml. of acetic acid is warned to 65° C. and 7.5 g. (0.089 mole) of cyclohexene is added, then 8.2 g. (0.089 mole) of dinitrogen tetraoxide diluted with 20 ml. of acetic acid is added dropwise. After stirring for about 3 hours, the reaction mixture is poured into cold water, and the solid precipitate is collected and washed with water and petroleum ether. The product is recrystallized from a mixture of N,N-dimethylformamide and water and from glyme and water. The product is 4-(2-nitro-3-benzofuranyl)benzoic acid, m.p. 274°–278° C.

| Analysis: | % C | % H | % N |
|---|---|---|---|
| Calculated for C₁₅H₉NO₅: | 63.6; | 3.2; | 4.9 |
| Found: | 63.2; | 3.2; | 5.2. |

Step E

Using the method of Example 1, Step A, 4-(2-nitro-3-benzofuranyl)benzoic acid is reacted with thionyl chloride to provide the corresponding benzoyl chloride, which is further reacted with sodium azide to provide the azide intermediate.

Step F

Using the method of Example 1, Step B, the azide intermediate of Step E above is converted to 4-(2-nitro-3-benzofuranyl)phenyl isocyanate.

Step G

Using the method of Example 25, 4-(2-nitro-3-benzofuranyl)phenyl isocyanate is reacted with n-propylamine to provide 1-(1-propyl)-3-[4-(2-nitro-3-benzofuranyl)phenyl]urea having the structure

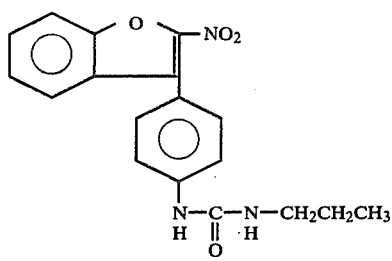

EXAMPLE 45

Reacting 5-(α-chloroacetamido)-2-nitro-3-phenylbenzofuran, the product of Example 11, by refluxing with a slight excess of piperidine provides 2-nitro-3-phenyl-5-[α-(1-piperidino)acetamido]benzofuran, m.p. 165°–167° C., after recrystallizing from aqueous isopropanol.

| Analysis: | % C | % H | % N |
|---|---|---|---|
| Calculated for $C_{21}H_{21}N_3O_4$: | 66.5; | 5.6; | 11.1 |
| Found: | 66.5; | 5.5; | 11.3. |

What is claimed is:
1. A compound of the formula

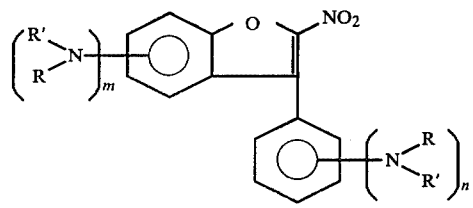

wherein
m and n are zero or one and the sum of m and n is one,
R is hydrogen or lower alkyl,
R' is R,

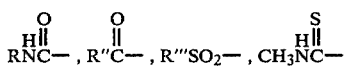

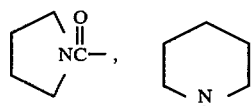

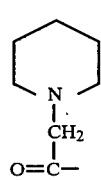

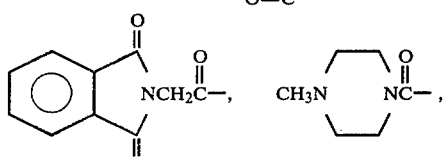

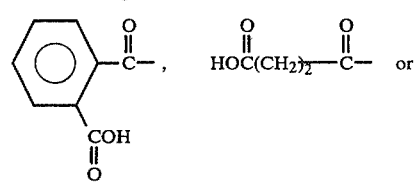

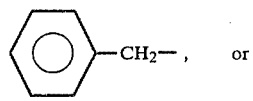

R and R' together form $(CH_3)_2N-N=$,

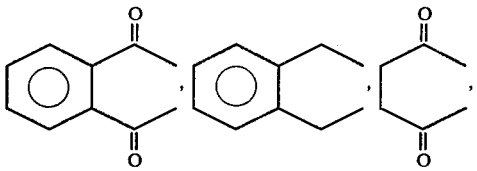

or complete a pyrrole or pyrrolidine ring through the nitrogen atom to which they are bonded,
R" is R, lower alkoxy, $CF_3-$ or $ClCH_2-$ and
R''' is lower alkyl or $CF_3-$, and pharmaceutically acceptable salts thereof.

2. A compound according to claim 1 in which R is hydrogen.

3. A compound according to claim 1 in which m is one.

4. A compound according to claim 1 in which R is hydrogen and R' is alkyl.

5. A compound according to claim 1 in which R is hydrogen and R' contains a carbonyl group which is bonded to the nitrogen atom of the formula.

6. A compound according to claim 1 in which R is hydrogen and R' contains a sulfonyl group which is bonded to the nitrogen atom of the formula.

7. A compound according to claim 1 in which R and R' together with the nitrogen atom to which they are bonded form a cyclic group.

8. A compound according to claim 3 in which R is hydrogen and R' is hydrogen or lower alkyl.

9. 5-Amino-2-nitro-3-phenylbenzofuran according to claim 8.

10. 7-Amino-2-nitro-3-phenylbenzofuran according to claim 8.

11. 5-Methylamino-2-nitro-3-phenylbenzofuran according to claim 8.

12. A compound according to claim 3 in which R is hydrogen and R' is

wherein R" is hydrogen, lower alkyl, lower alkoxy, $CF_3$ or $ClCH_2$.

13. 7-Acetamido-2-nitro-3-phenylbenzofuran according to claim 12.

14. 5-Acetamido-2-nitro-3-phenylbenzofuran according to claim 12.

15. 5-Formamido-2-nitro-3-phenylbenzofuran according to claim 12.

16. 6-Acetamido-2-nitro-3-phenylbenzofuran according to claim 12.

17. 7-(Methyl carbamoyl)-2-nitro-3-phenylbenzofuran according to claim 12.

18. 5-(Ethyl carbamoyl)-2-nitro-2-phenylbenzofuran according to claim 12.

19. 5-(α-Chloroacetamido)-2-nitro-3-phenylbenzofuran according to claim 12.

20. 2-Nitro-3-phenyl-5-trifluoroacetamidobenzofuran according to claim 12.

21. 2-Nitro-3-phenyl-5-ureidobenzofuran according to claim 3.

22. 5-Methylureido-2-nitro-3-phenylbenzofuran according to claim 3.

23. 2-Nitro-3-phenyl-5-(n-propyl)ureidobenzofuran according to claim 3.

24. A method for inhibiting or arresting the growth of bacteria comprising contacting said bacteria with a compound according to claim 1 in an amount sufficient to inhibit the growth of said bacteria.

* * * * *